United States Patent [19]

Nalepa

[11] Patent Number: 4,475,004

[45] Date of Patent: Oct. 2, 1984

[54] PREPARATION OF ALKANEDIOLS

[75] Inventor: Christopher J. Nalepa, Baton Rouge, La.

[73] Assignee: Ethyl Corporation, Richmond, Va.

[21] Appl. No.: 564,087

[22] Filed: Dec. 21, 1983

[51] Int. Cl.$^3$ .................... C07C 29/132; C07C 33/26; C07C 67/00; C07C 59/245
[52] U.S. Cl. ............................ 568/865; 260/465.6; 560/263; 562/582; 568/807
[58] Field of Search ............. 568/865, 807; 562/582; 560/263; 260/465.6

[56] References Cited

U.S. PATENT DOCUMENTS

| | | | |
|---|---|---|---|
| 2,546,019 | 3/1951 | Smith | 568/865 |
| 2,888,492 | 5/1959 | Fischer et al. | 568/865 |
| 3,760,011 | 9/1973 | Robinson et al. | 568/865 |
| 4,146,741 | 3/1979 | Prichard | 568/865 |

FOREIGN PATENT DOCUMENTS

| | | | |
|---|---|---|---|
| 527170 | 7/1956 | Canada | 568/865 |
| 673367 | 10/1963 | Canada | 568/865 |

OTHER PUBLICATIONS

James M. Watson, "Butane-1,4-diol From Hydrolytic Reduction of Furan", Ind. Eng. Chem. Prod. Res. Develop. 12 (4), 310–311, (1973).

*Primary Examiner*—J. E. Evans
*Attorney, Agent, or Firm*—Donald L. Johnson; John F. Sieberth; Teresa M. Stanek

[57] ABSTRACT

Disclosed is an improved process for producing alkanediols by the hydrolytic reduction of hydrolytically reducible furans. The improvement comprises utilizing a supported nickel catalyst, and trihaloacetic acid, preferably trifluoracetic acid or trichloroacetic acid or a mixture thereof as a promoter for the hydrolytic reduction. The hydrolytic reduction is conducted in an aqueous medium at elevated temperatures and elevated pressures.

20 Claims, No Drawings

PREPARATION OF ALKANEDIOLS

FIELD OF THE INVENTION

This case relates to a process for the preparation of alkanediols from furans.

BACKGROUND OF THE INVENTION

Furan has been hydrogenated in a neutral or weakly acid aqueous system in the presence of a nickel catalyst as shown by Russian Pat. No. 114,928 (1958) to P.A. Moshkin et al. to produce 1,4-butanediol, tetrahydrofuran and small amounts of butanol. One example shows the inclusion of a small amount of formic acid in the reaction mixture. James M. Watson, Ind. Eng. Chem. Prod. Res. Develop 12 (4) 310-311 (1973) shows the same general reaction where acetic acid is present in the reaction mixture. In both processes, the yield of 1,4-butanediol is not as high as could be desired and unwanted by-products are produced, such as the mono- and diformate, and mono- and diacetate esters of 1,4-butanediol. These esters have boiling points quite close to the boiling point of 1,4-butanediol itself and it is expensive and difficult to distill them off; in fact, the diacetate ester of 1,4-butanediol has the same boiling point as 1,4-butanediol and cannot be separated by distillation. Accordingly, the 1,4-butanediol produced by these processes contains the esters as impurities. Pure, "polymer grade" 1,4-butanediol is necessary in the manufacture of useful high molecular weight polyesters such as from terephthalic acid. Therefore, the impure diol produced by the above-mentioned prior art processes cannot be used directly.

A welcome contribution to the art would be a process that produces alkanediols—e.g., 1,4-butanediol—in good yields, without substantial impurities which cannot be easily separated from the highly desired alkanediols.

THE INVENTION

This invention provides an improved process for the production of alkanediols in which the two hydroxy groups resulting from the hydrolytic reduction are bonded to different carbon atoms which are separated by two other carbon atoms—i.e., the two hydroxy groups resulting from the hydrolytic reduction are in a "1,4" position relative to each other—by the hydrolytic reduction of hydrolytically reducible furans at elevated temperatures and elevated pressures using a supported metal catalyst. The improvement comprises conducting the hydrolytic reduction in an aqueous medium utilizing a supported nickel catalyst, and a trihaloacetic acid, preferably trifluoracetic acid or trichloroacetic acid or a mixture thereof as promoter for the hydrolytic reduction.

The hydrolytically reducible furans utilizable in the process of this invention are furan and any substituted furan whose substituent(s) are inert under the reaction conditions. In general the furans are represented by the formula:

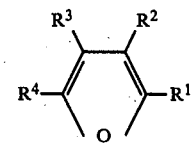

wherein $R^1$, $R^2$, $R^3$ and $R^4$ are the same or different aliphatic or aromatic group(s) or hydrogen atom(s). Examples of the substituent groups include, but are not limited to: hydrocarbyl groups, such as, alkyl, aryl, and the like; carboxylic acid derived groups; alkanol derived groups, such as, hydroxyalkyl, e.g., —$CH_2OH$, and the like; alkenyl derived groups, such as, those groups derived from, for example, acrylonitrile, e.g., —CH=CH—CN, and the like. Examples of substituted furans include, but are not limited to: 2-methylfuran, 2,5-dimethylfuran, 2,5-diphenylfuran, 3-methylfuran, 2-acetylfuran, 3,4-bis(acetoxymethyl)furan, 2-furanacrylonitrile, 3,4-furandicarboxylic acid, 2,5-furandimethanol, 3-furanmethanol, and the like.

The furan used will, of course, determine the alkanediol product obtained by the process of this invention. Preferably, the process of this invention is utilized to produce 1,4-butanediol and substituted 1,4-butanediols. Thus, for example, 1,4-butanediol is obtained from furan; 1-methyl-1,4-butanediol (1,4-pentanediol) from 2-methylfuran; 1,4-dimethyl-1,4-butanediol (2,5-hexanediol) from 2,5-dimethylfuran; and the like.

The catalysts utilized are composed of nickel (Ni) on inert carriers or supports. Any carrier or support may be used as long as it is inert under the reaction conditions. Examples of these supports may include, for example, $Al_2O_3$—$SiO_2$, diatomaceous earth, finely divided silica, activated carbon, and the like. A preferred carrier is $Al_2O_3$—$SiO_2$. The amount of nickel on the support is not critical to the reaction, however, catalysts containing about 20% by weight to about 80% by weight of nickel, based on the weight of the catalyst are preferred, with about 50% by weight to about 70% by weight being more preferred, and about 65% be weight being most preferred. Supported nickel catalysts are commercially available. For example, a catalyst comprising 65% nickel on an $Al_2O_3$—$SiO_2$ support is available under the designation Ni-5132P from Harshaw Chemical Company. The catalyst to furan weight ratio is within the range of from about 1:3 (catalyst:furan) to about 1:50 with from about 1:7 to about 1:30 being preferred and about 1:15 being more preferred. The catalyst is used with a trihaloacetic acid, preferably trifluoroacetic acid or trichloroacetic acid or a mixture thereof as the promoter for the hydrolytic reduction. The weight ratio of promoter to catalyst based upon the nickel content of the catalyst is within the range of from about 1:1 (promoter:catalyst) to about 1:2.5 with about 1:1.6 being preferred.

The hydrolytic reduction is conducted in an aqueous medium with water being the preferred medium. The amount of water can vary widely, but preferably the weight ratio of water to furan is within the range of from about 1:4 to about 2:1 (water:furan) with about 1:2 to about 1:1 being more preferred.

As stated above, the reaction is conducted at elevated temperatures and elevated pressures. The temperature is within the range of from about 175° C. to about 225° C., with about 190° C. to about 210° C. being preferred, and with about 200° C. being more preferred. The reaction pressure can vary during the course of the hydrolytic reduction, but is preferably within the range of from about 500 to about 1500 psig, with from about 700 to about 1100 psig being preferred, and with about 900 to about 1100 psig being more preferred.

The alkanediols may be separated by techniques well known to those skilled in the art, such as, for example, distillation, vacuum distillation (e.g., rotary evaporation) and the like.

Particularly good yields of 1,4-butanediol are obtained when 1.0 g of promoter and 2.5 g of a 65% Ni catalyst supported on $Al_2O_3$—$SiO_2$ are utilized per 37.5 g of furan at a temperature of about 200° C. and a reaction pressure of about 900 to about 1100 psig in the presence of about 20.5 g of water.

The following examples serve to illustrate this invention and should not be construed as limiting the invention in any way.

GENERAL PROCEDURE

Unless noted otherwise, a 300 mL autoclave was charged with water (20.5 g), catalyst (2.5 g 65% nickel on $Al_2O_3$—$SiO_2$ Harshaw Ni-5132P), acid promoter (1.0 g, trifluoroacetic acid), and furan (37.5 g). The autoclave was flushed twice with approximately 100 psig $H_2$ and then pressure tested at approximately 500 psig $H_2$. The autoclave was then heated to approximately 200° C. with stirring under approximately 500 psig $H_2$. At approximately 190° C. (approximately 45 minutes; e.g., 30–50 minutes, i.e., the warm up time after heating had commenced), the reactor was charged to approximately 1100 psig with $H_2$. The reaction temperature quickly rose to 200° C. and the autoclave was cooled with water to prevent a temperature overshoot. When the pressure in the autoclave dropped to approximately 900±50 psig $H_2$, it was recharged to approximately 1100±50 psig $H_2$. After approximately two hours, $H_2$ uptake stopped. The autoclave was cooled to approximately 30° C. (e.g., 27° C. -33° C.) and disconnected from the $H_2$ source while still under pressure. The reactor was then cooled for approximately ½ hour in an ice bath, vented and opened. An aliquot of the reaction mixture was centrifuged and a measured amount of supernatant was mixed with a measured amount of cyclohexanol. VPC analysis was conducted on this mixture to determine the relative amounts (in weight %) of the reaction products.

The VPC conditions were 10% SE-52, ⅛"×12'; starting temperature 60° C., held for 3 minutes and then brought to 160° C. at 20° per minute and then held at 160° C.

CONTROL

A 300 mL autoclave liner was charged with water (20.5 g), furan (37.5 g), and a 65% nickel catalyst supported on $Al_2O_3$—$S_2O_2$ (Harshaw Ni-5132P, 2.5 g.). No promoter was used in this reaction. The autoclave was pressure tested at 550 psig $H_2$ and then heated to 200° C. (approximately one hour). The $H_2$ uptake stopped after 1.5 hours, during this period the $H_2$ pressure was maintained at 900–1100 psi. A total of 1550 psig $H_2$ was absorbed. The autoclave was cooled to 0° C. and vented.

Following the above procedure, a control reaction was run without the use of a promoter.

VPC analysis showed only a trace (estimate of about 0.1 wt %, 0.2 g) of 1,4-butanediol was produced. Other reaction products were 31.99 g of tetrahydrofuran and 1.96 g of n-butanol. Furan, 2.78 g, was recovered giving a conversion of 92.6%. The carbon closure was 95%.

EXAMPLES 1-5

The results obtained by following the foregoing procedure utilizing the promoter of this invention, Examples 1, and promoters not of this invention, comparative Examples 2-5, are reported in Table I. The reaction time approximately 2 hours. In Example 2, the reaction pressure was within the range of about 750 to about 1100 psig. In Table I the following abbreviations are used: Rxn=reaction, BD=1,4-butanediol, THF=tetrahydrofuran, and nBuOH=n-butanol. The yield of 1,4-butanediol (BD) as based upon converted starting furan was determined by the following formula:

$$\frac{\text{Moles BD}}{(\text{conversion}) (\text{moles furan})} \times 100$$

wherein the moles of furan is the amount of furan at the start of the reduction process.

The percent conversion is determined by the following formula:

$$\frac{x-y}{x} \times 100$$

wherein x is the amount of furan in grams at the start of the reaction and y is the amount of furan left at the end of the reaction.

The percent carbon-closure was determined by the following formula:

$$\frac{p}{q} \times 100$$

wherein p is the total number of moles of all products formed in the reaction and q is the moles of furan at the start of the reaction.

TABLE I

Hydrolytic Reduction of Furan Using Different Acidic Promoters

| Example No. | Acid Promoter | Initial pH | Rxn[1] Time (Hrs) | Conversion (%) | BD (g) | THF (g) | nBuOH (g) | BD Yield (%) | BD/THF wt ratio | Closure (%) |
|---|---|---|---|---|---|---|---|---|---|---|
| 1 | $CF_3CO_2H$ | 0.56 | 2 | 98.5 | 13.3 | 20.9 | 1.2 | 27.2 | 0.64 | 84 |
| Comparative Example No. | | | | | | | | | | |
| 2 | $CH_3CO_2H$ | 2.42 | 2 | 98.9 | 6.7 | 27.0 | 2.2 | 13.7 | 0.25 | 89 |
| 3 | $HCO_2H$[2] | 1.86 | 2 | >99 | 0 | 32.6 | 4.2 | 0 | 0 | 93 |
| 4 | $HO_2C(CH_2)_4CO_2H$ | 2.44 | 2 | >99 | 4.2 | 29.5 | 1.4 | 8.5 | 0.14 | 87 |

TABLE I-continued

Hydrolytic Reduction of Furan Using Different Acidic Promoters

| | Acid Promoter | Initial pH | Rxn[1] Time (Hrs) | Conversion (%) | BD (g) | THF (g) | nBuOH (g) | BD Yield (%) | BD/THF wt ratio | Closure (%) |
|---|---|---|---|---|---|---|---|---|---|---|
| 5 | HO₂CCO₂H | 0.82 | 2 | >99 | 3.4 | 30.6 | 3.5 | 6.8 | 0.11 | 93 |

[1] 1 hour heat up time not included
[2] Acid apparently decomposed under the reaction conditions The data in Table I clearly demonstrate that good yields of 1,4-butanediol were obtained with the promoters of the catalyst/promoter systems of this invention whereas use of promoters not of this invention resulted in poor yields of 1,4-butanediol.

The foregoing disclosure and description of the invention is illustrative and explanatory thereof and various changes in the illustrated process may be made within the scope of the appended claims without departing from the spirit of the invention.

I claim:

1. In a process for producing alkanediols by the hydrolytic reduction of hydrolytically reducible furans at elevated temperatures and elevated pressures using a supported metal catalyst, said alkanediols having the two hydroxy groups resulting from said hydrolytic reduction bonded to different carbon atoms which are separated from each other by two other carbon atoms, the improvement which comprises conducting the hydrolytic reduction in an aqueous medium utilizing a supported nickel catalyst, and trihaloacetic acid or a mixture thereof as a promoter for the hydrolytic reduction.

2. The process of claim 1 wherein said catalyst contains about 20 to about 80% by weight of nickel.

3. The process of claim 1 wherein said catalyst comprises 65% by weight of nickel supported on Al₂O₃—SiO₂.

4. The process of claim 1 wherein said promoter is trichloroacetic acid.

5. The process of claim 1 wherein said promoter is trifluoroacetic acid.

6. The process of claim 1 wherein said catalyst to said furan weight ratio is within the range of from about 1:3 to about 1:50.

7. The process of claim 1 wherein said promoter to said catalyst weight ratio based upon the nickel content of the catalyst is within the range of from about 1:1 to about 1:2.5.

8. The process of claim 1 wherein said furan is a hydrocarbyl substituted furan.

9. The process of claim 1 wherein said furan is furan, and said alkanediol is 1,4-butanediol.

10. The process of claim 1 wherein for a predominant time during the course of said hydrolytic reduction said temperature is within the range of from about 175° to about 225° C. and said pressure is within the range of from about 500 to about 1500 psig.

11. The process of claim 1 wherein for a predominant time during the course of said hydrolytic reduction said temperature is within the range of from about 190° to about 210° C. and said pressure is within the range of about 700 to about 1100 psig.

12. The process of claim 11 wherein said temperature is about 200° C., and said pressure is within the range of about 900 to about 1100 psig.

13. The process of claim 1 wherein said aqueous medium is water and wherein said water to said furan weight ratio is within the range of from about 1:4 to about 2:1.

14. In a process for producing alkanediols by the hydrolytic reduction of hydrolytically reducible furans at elevated temperatures and elevated pressures using a metal catalyst, said alkanediols having the two hydroxy groups resulting from said hydrolytic reduction bonded to different carbon atoms which are separated from each other by two other carbon atoms, the improvement which comprises conducting the hydrolytic reduction in a water medium utilizing a supported nickel catalyst containing about 20 to about 80% by weight of nickel, and trihaloacetic acid or a mixture thereof as promoter for the hydrolytic reduction, said catalyst to said furan weight being in a ratio within the range of from about 1:3 to about 1:50, said promoter to said catalyst being in a weight ratio based upon the nickel content of the catalyst within the range of from about 1:1 to about 1:2.5, and for a predominant time during the course of said hydrolytic reduction said water to said furan being in a weight ratio within the range of from about 1:4 to about 2:1, said temperature being within the range of from about 175° to about 225° C. and said pressure being within the range of from about 500 to about 1500 psig.

15. The process of claim 14 wherein Al₂O₃—SiO₂ is the support for said catalyst.

16. The process of claim 17 wherein said promoter is trichloroacetic acid, said furan is furan, said alkanediol is 1,4-butanediol and Al₂O₃—SiO₂ is the support for said catalyst.

17. The process of claim 14 wherein said promoter is trifluoroacetic acid, said furan is furan and Al₂O₃—SiO₂ is the support for said catalyst.

18. In a process for producing a 1,4-butanediol by the hydrolytic reduction of hydrolytically reducible furans at elevated temperatures and elevated pressures using a supported metal catalyst, said alkanediols having the two hydroxy groups resulting from said hydrolytic reduction bonded to different carbon atoms which are separated from each other by two other carbon atoms, the improvement which comprises conducting the hydrolytic reduction in a water medium utilizing a supported nickel catalyst containing about 65% by weight of nickel, and trihaloacetic acid or a mixture thereof as promoter for the hydrolytic reduction, said catalyst to said furan weight ratio being within the range of about 1:7 to about 1:30, said promoter to said catalyst being in a weight ratio based upon the nickel content of the catalyst of about 1:1.6, said water to said furan being in a weight ratio within the range of about 1:2 to about 1:1, and for a predominant time during the course of said hydrolytic reduction said temperature being within the range of about 190° C. to about 210° C. and said pressure being within the range of about 700 to about 1100 psig.

19. The process of claim 18 wherein said promoter is trichloroacetic acid or trifluoroacetic acid, said furan is furan, said alkanediol is 1,4-butanediol and Al₂O₃SiO₂ is the support for said catalyst.

20. The process of claim 19 wherein the pressure is within the range of about 900 to about 1100 psig.

* * * * *

UNITED STATES PATENT AND TRADEMARK OFFICE
CERTIFICATE OF CORRECTION

PATENT NO. : 4,475,004
DATED : October 2, 1984
INVENTOR(S) : Christopher J. Nalepa It is certified that error appears in the above-identified patent and that said Letters Patent is hereby corrected as shown below:

Column 2, line 42, reads "be weight" and should read -- by weight --.

Column 3, line 38, reads "uptake stopped" and should read -- uptake essentially stopped --.

Column 4, lines 21 and 22, read "time approximately" and should read -- time was approximately --.

Table I, line 12, under Conversion (%) Example No. 2, reads "98.9" and should read -- 98.8 --.

Column 6, line 65, reads "$Al_2O_3SiO_2$" and should read -- $Al_2O_3-SiO_2$ --.

Signed and Sealed this

Twenty-third Day of April 1985

[SEAL]

Attest:

DONALD J. QUIGG

Attesting Officer

Acting Commissioner of Patents and Trademarks